(12) United States Patent
Gupta et al.

(10) Patent No.: US 11,850,172 B2
(45) Date of Patent: Dec. 26, 2023

(54) HIGH RETENTION DRAINAGE DEVICE

(71) Applicant: Boston Scientific Scimed, Inc., Maple Grove, MN (US)

(72) Inventors: Saurav V. Gupta, Medway, MA (US); Marc A. Barthet, Marseilles (FR); Jean-Michel Gonzalez, Fuveau (FR); Camron Hagemeyer, Bloomington, IN (US); Darren G. Curran, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 95 days.

(21) Appl. No.: 17/222,735

(22) Filed: Apr. 5, 2021

(65) Prior Publication Data
US 2021/0307943 A1 Oct. 7, 2021

Related U.S. Application Data

(60) Provisional application No. 63/005,936, filed on Apr. 6, 2020.

(51) Int. Cl.
*A61F 2/90* (2013.01)
*A61F 2/852* (2013.01)

(52) U.S. Cl.
CPC .............. *A61F 2/90* (2013.01); *A61F 2/852* (2013.01); *A61F 2220/0008* (2013.01)

(58) Field of Classification Search
CPC ....... A61F 2/848; A61F 2/90; A61F 2230/001
See application file for complete search history.

(56) References Cited

U.S. PATENT DOCUMENTS

2013/0012969 A1  1/2013  Shin
2018/0280669 A1  10/2018  Shlomovitz et al.
2019/0099589 A1*  4/2019  Walsh ................. A61B 17/1114

FOREIGN PATENT DOCUMENTS

WO  2019097424 A2  5/2019

OTHER PUBLICATIONS

International Search Report and Written Opinion for the International Patent Application No. PCT/US2021/025802, dated Jul. 27, 2021, 17 pages.

* cited by examiner

*Primary Examiner* — William H Matthews
(74) *Attorney, Agent, or Firm* — Seager, Tufte & Wickhem, LLP

(57) ABSTRACT

The present disclosure relates generally to the field of medical devices. In particular, the present disclosure relates to medical devices for facilitating the flow of fluids and materials in and/or between adjacent body lumens, for example, a stent which maintains an open flow passage between body lumens. In one example, a stent may comprise an elongate body configured to be expandable between a first constrained configuration and a second unconstrained configuration. In the unconstrained configuration, the body may have a first retention member, a second retention member, and a cylindrical saddle region defining a lumen extending along a longitudinal axis therebetween. The first retention member or the second retention member, or both, may comprise a double-walled flange with an axially inward wall and axially outward wall, a portion of the inward wall bending towards a vertical center plane of the saddle region along the longitudinal axis.

20 Claims, 5 Drawing Sheets

HIGH RETENTION DRAINAGE DEVICE

CROSS REFERENCE TO RELATED APPLICATIONS

This application claims the benefit of priority under 35 U.S.C. § 119 to U.S. Provisional Patent Application Ser. No. 63/005,936, filed on Apr. 6, 2020, which is incorporated by reference in its entirety for all purposes.

FIELD

The present disclosure relates generally to the field of medical devices. In particular, the present disclosure relates to medical devices for facilitating the flow of fluids and materials between adjacent body lumens, such as a stent which maintains an open flow passage between or within body lumens.

BACKGROUND

Placement of a self-expanding stent (e.g., self-expanding metal stent or SEMS) within an anatomical area (e.g., body lumen, passage, vessel, duct, etc.) may enable fluid communication from one area to another. For example, a stent may enable flow of material from one body lumen to another.

However, available stents may carry various disadvantages. For example, stents may be more likely to dislodge or migrate from a desired placement, such as in response to forces generated by a patient's motion, or may fail to provide enough or provide too much retentive force for a given use.

Accordingly, a variety of advantageous medical outcomes may be realized by the devices and/or methods of the present disclosure.

SUMMARY

In one aspect, a stent may comprise an elongate body configured to be expandable between a first constrained configuration and a second unconstrained configuration. The elongate body in the unconstrained configuration may include a first retention member, a second retention member, and a cylindrical saddle region extending along a longitudinal axis therebetween. The cylindrical saddle region may define a lumen extending along the longitudinal axis. The first retention member or the second retention member, or both, may comprise a double-walled flange having an axially inward wall, an axially outward wall, and a radially outwardmost edge extending therebetween. At least a portion of the inward wall may bend towards a vertical center plane of the cylindrical saddle region along the longitudinal axis.

In the described and other aspects of the present disclosure, the inward wall and the outward wall of the first retention member or the second retention member, or both, may comprise non-parallel surfaces. At least a portion of the outward wall may bend away from the vertical center plane of the cylindrical saddle region along the longitudinal axis. The outward wall may comprise a concave portion bending away from the vertical center plane of the cylindrical saddle region along the longitudinal axis. The inward wall or the outward wall, or both, may comprise a straight edge. The inward wall may comprise a convex portion bending away from the vertical center plane of the cylindrical saddle region along the longitudinal axis. The outward wall may comprise a convex portion bending toward the vertical center plane of the cylindrical saddle region along the longitudinal axis. An axially outermost end of the first retention member or an axially outermost end of the second retention member, or both, may extend away from the vertical center plane of the cylindrical saddle region into a lip. The lip may define a lumen of the double-walled flanges. The flange lumens may be contiguous with the cylindrical saddle region lumen. The lip may comprise an interior diameter of the flange lumens equal to or wider than an interior diameter of the cylindrical saddle region lumen. The radially outwardmost edge may comprise a diameter greater than a diameter of the cylindrical saddle region. The radially outwardmost edge may comprise a cylindrical portion parallel to the longitudinal axis. An interior radius of curvature between the inward wall and the radially outwardmost edge may be greater than, equal to or smaller than an interior radius of curvature between the radially outwardmost edge and the outward wall. The radially outwardmost edge may be offset from a vertical plane along the longitudinal axis between a beginning of the inward wall and an ending of the outward wall. The elongate body may comprise a braid of one or multiple wires. The stent may comprise a circumferential covering extending fully or partially along a length of the elongate body.

In one aspect, a stent may comprise a tubular structure having a constrained configuration and an expanded configuration. The tubular structure in the expanded configuration may include a first end of the tubular structure expanded into a first double-walled flange, a second end of the tubular structure expanded into a second double-walled flange, and a central region extending along a longitudinal axis therebetween. The central region may define a lumen extending along the longitudinal axis. The first double-walled flange or the second double-walled flange, or both, may comprise an axially inward wall and an axially outward wall. At least a portion of the inward wall may bend towards a vertical center plane of the central region along the longitudinal axis. A cross-sectional profile of the first double-walled flange or the second double-walled flange, or both, along a plane parallel to the longitudinal axis, may be asymmetrical.

In the described and other aspects of the present disclosure, the inward wall and the outward wall of the first retention member or the second retention member, or both, may comprise non-parallel surfaces. The inward wall may comprise a first curved portion bending toward the vertical center plane of the central region along the longitudinal axis, the inward wall may comprise a second curved portion bending away from the vertical center plane of the central region along the longitudinal axis, or the inward wall may comprise both of the first curved portion and second curved portion. The inward wall or the outward wall, or both, may comprise a straight edge.

In one aspect, a stent may comprise a cylindrical body having a constrained configuration and an expanded configuration. In the expanded configuration, the cylindrical body may comprise a first retention member, a second retention member, and a saddle region extending along a longitudinal axis between the first retention member and the second retention member. The saddle region may define lumen extending along the longitudinal axis. The first retention member or the second retention member, or both, may comprise double-walled flanges including an axially inward wall and an axially outward wall. At least a portion of the inward wall may bend towards a vertical center plane of the saddle region along the longitudinal axis. The inward wall and the outward wall of the first retention member or the second retention member, or both, may comprise non-parallel surfaces.

In the described and other aspects of the present disclosure, the inward wall may comprise a first curved portion bending toward the vertical center plane of the saddle region along the longitudinal axis, the inward wall may comprise a second curved portion bending away from the vertical center plane of the saddle region along the longitudinal axis, or the inward wall may comprise both of the first curved portion and second curved portion. In the above aspects and other aspects of the present disclosure, the same or different inward and outward wall features may be applied to a double-walled flange of the first retention member, the second retention member, or both. That is, a stent according to aspects of the present disclosure may have a double-walled flange on either or both of the first and second retention members, and the axially inward and outward walls of flanges, when occurring with respect to both retention members, may be configured similarly or differently.

BRIEF DESCRIPTION OF THE DRAWINGS

Non-limiting examples of the present disclosure are described with reference to the accompanying figures, which are schematic and not intended to be drawn to scale. In the figures, each identical or nearly identical component illustrated is typically represented by a single numeral. For purposes of clarity, not every component is labeled in every figure, nor is every component in each embodiment of the disclosure shown where illustration is not necessary to allow those of skill in the art to understand the disclosure. In the figures.

DETAILED DESCRIPTION

Figure 1:
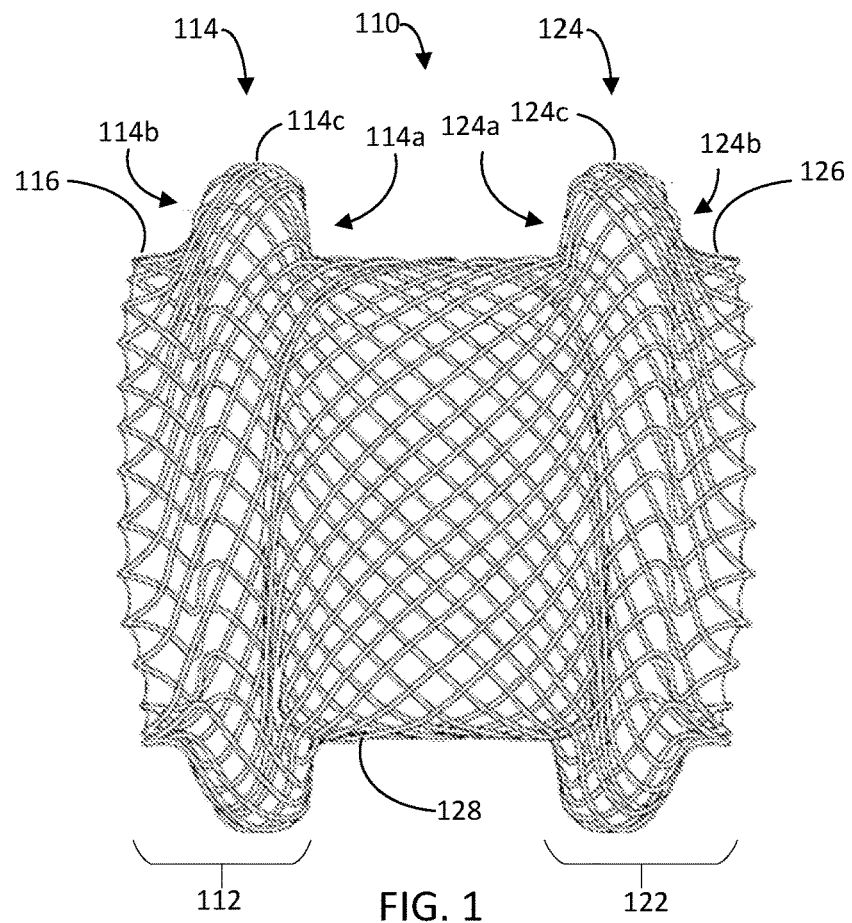
FIG. 1 illustrates a side view of a medical device according to one or more embodiments described herein.

The present disclosure is not limited to the particular embodiments described. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to medical devices (e.g., stents, etc.) and systems for drainage of the gallbladder, pseudocysts, and/or gastrojejunostomy, or the like, it should be appreciated that such medical devices may be used in a variety of medical procedures (e.g., external biliary drain conversion, enteroenterostomy, gastroduodenostomy and gastroileostomy, etc.) to establish and/or maintain a temporary or permanent open flow or drainage passage from or between a variety of body organs, lumens, ducts, vessels, fistulas, cysts and spaces (e.g., the dermis, stomach, duodenum, jejunum, small intestine, gallbladder, kidneys, pancreas, biliary/pancreatic trees, bladder, ureter, abscesses, walled-off pancreatic necrosis (WOPN), bile ducts, etc.). The devices may be inserted via different access points and approaches, e.g., percutaneously, endoscopically, laparoscopically or some combination thereof. The medical devices disclosed herein are self-expanding, but in other embodiments the medical device may be expandable by other means, including, e.g., a balloon catheter. Moreover, such medical devices are not limited to drainage, but may facilitate access to organs, vessels or body lumens for other purposes, such as creating a path to divert or bypass fluids or solids from one location to another, removing obstructions and/or delivering therapy, including non-invasive or minimally invasive manipulation of the tissue within the organ and/or the introduction of pharmacological agents via the open flow passage.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

In embodiments, the present disclosure relates to a medical device (e.g., self-expanding metal stent and/or a duodenal exclusion device, etc.) configured to extend between first and second body lumens and assist with apposing or maintaining apposition of respective layers (e.g., muscularis layers) of each body lumen to establish a temporary, long term or permanent open flow or access passage therebetween. One or both of first and second retention members at opposing ends of the stent, as described herein, such as flanges, may be double-walled and include one or more non-perpendicular surfaces of an axially inward and axially outward wall of the flange, the walls oriented with respect to a cylindrical saddle region extending along a longitudinal axis between the flanges. Such a configuration of non-perpendicular surface may reduce migration of the medical device with respect to the tissue(s) between the first and second body lumens, when compared, for example, to a corresponding retention member with only perpendicular surfaces. Additionally, or alternatively, retention members, as double-walled flanges with one or more non-perpendicular surfaces, may be configured to provide more control over the resistance of the device being pulled out of its intended placement once deployed, e.g., resulting in higher pull-out forces as compared to a corresponding retention member with perpendicular surfaces. For example, a double-walled flanged with non-perpendicular surfaces may have a pull-out force above 4 N, 4.5 N, 5 N, 5.25 N, 5.5 N, 5.75 N, or 6 N, such as a pull-out force of 4.1 N, 4.2 N, 4.3 N, 4.4 N, 4.5 N, 4.6 N, 4.7 N, 4.8 N, 4.9 N, 5.0 N, 5.1 N, 5.2 N, 5.3 N, 5.4 N, 5.5 N, 5.6 N, 5.7 N, 5.75 N, 5.8 N, 5.9 N, 6.0 N, 6.1 N, 6.2 N, 6.3 N, 6.4 N, 6.5 N, 6.6 N, 6.7 N, 6.8 N, 6.9 N, 7.0 N, 7.1 N, 7.2 N, 7.3 N, 7.4 N, 7.5 N, 7.6 N, 7.7 N, 7.8 N, 7.9 N, 8.0 N, 8.1 N, 8.2 N, 8.3 N, 8.4 N, 8.5 N, 8.6 N, 8.7 N, 8.8 N, 8.9 N, or 9.0 N. In various embodiments, one or more non-perpendicular surfaces may also be configured to interact less traumatically with at least one tissue wall of the first and second body lumens (e.g., configuring an inward with a point of tissue contact having less surface area), as compared, for example, to a perpendicular surface or to another surface with at least one tissue-engaging element, such as a prong, barb, hook, or other like design.

Non-perpendicular surfaces of medical devices, such as of stents with retention members comprising axially inward and outward walls of double-walled flanges, may comprise one or more curved portions, straight portions, angled portions, or any combination thereof, wherein each portion may comprise an equal or a different length, angle, interior radius of curvature, directionality, interior angle, or other feature with respect to another portion. Surfaces of first retention members and second retention members may be the same or different. For example, each end of a medical device may be designed to improve the strength (e.g., resistance to pull-out or retentive strength, or resistance to radial compression or radial strength) of a medical device and provide a desired amount of linear apposing force when placed across tissue planes. Flange shapes may comprise one or more rolls and/or structural folds, for example, to create a double-walled flange structure. In various embodiments, flange shapes may comprise a plurality of inflection points, wherein an inflection point may be a point of a curve at which a change in direction of curvature occurs.

A medical device, such as a stent, may be formed of one or more filaments and/or surfaces. In various embodiments, one or multiple metal wires, braids of one or multiple wires, polymeric filaments, sheets, or a combination thereof may form a medical device. For example, a length of braid of one or multiple wires may form a medical device. A medical device may include one or more structural elements such as a strut, hoop, mesh, tessellating cell, or other unit. In many embodiments, a medical device may comprise a mesh, weave, and/or knit surface. A medical device may be formed, in various embodiments, of a shape memory material, such as nitinol.

Various embodiments of medical devices described herein may include a full or partial covering, coating, or other membrane over an interior, over an exterior of the devices, extending between structural elements, or any combination thereof. For example, a covering, coating, or other membrane may comprise silicone, a polymer, or a combination thereof. For example, a cover may comprise polyurethane, polytetrafluoroethylene, expanded polytetrafluoroethylene, polyvinylidene fluoride, an aromatic polycarbonate-based thermoplastic urethane, and/or other like materials. A cover may be applied by dip coating, roll coating, painting, spraying, other known disposition method, or a combination thereof. A covering, coating, or other membrane may inhibit tissue growth and/or minimize fluid leakage from within and/or without the medical device.

A covering, coating, or other membrane may extend fully or partially over a medical device. For example, a first retention member, a second retention member, a saddle region extending between a first retention member and a second retention member, or a combination thereof may comprise a solid covering, a porous covering, or other configuration of covering. In some embodiments, such as stents having a cylindrical saddle region and double-walled flanges as first and second retention members, a circumferential covering or coating may be applied to cover the full length of the stent, or a partial length of the stent. For example, a partial coating may cover the full length of the saddle region, but not the flanges. Embodiments are not limited herein.

Various embodiments described herein may comprise one or more additional features designed to engage at least one tissue layer. For example, embodiments may include one or more textured surfaces, prongs, or other tissue-engaging elements along a first retention member, a second retention member, or any combination thereof.

Referring to FIG. 1, in one embodiment, a stent of the present disclosure may include an elongate body or tubular structure 110 forming a lumen and comprising a first portion, a second portion, a length and a diameter. The elongate body 110 may be covered, uncovered, or a combination thereof. The elongate body 110 may include a constrained configuration (e.g., unexpanded or delivery configuration; not shown), and an expanded or unconstrained configuration (e.g., foreshortened or deployed configuration, as shown in FIG. 1). The elongate body may be configured to be expandable between the constrained configuration and the unconstrained configuration. In the unconstrained configuration, the first portion 112 of the elongate body is radially expandable into a first retention member 114, and the distal portion 122 of the elongate body is radially expandable into a second retention member 124. In some embodiments, the elongate body 110 in the constrained configuration, may comprise a diameter in the range inclusive of 2-6 mm, or 3-5 mm. For example, a stent may have a diameter in a constrained configuration of 10 Fr or 3.5 mm. In some embodiments, the elongate body 110 in the constrained configuration may have a length within the range inclusive of 40-150 mm. For example, a stent in a constrained configuration may have a length within the range inclusive of 40-100 mm. In some embodiments, a stent in the constrained configuration may have a length within the range inclusive of 40-80 mm.

A central region may extend along a longitudinal axis of a stent between retention members. For example, as shown in FIG. 1, a central region may comprise a cylindrical saddle region 128 extending along the longitudinal axis of the stent between the first retention member 114 and the second retention member 124. The cylindrical saddle region 128 may comprise a tubular structure or a cylindrical body, defining or otherwise comprising a lumen extending therethrough along the longitudinal axis, or a similar structure. The cylindrical saddle region 128 may comprise a length and a diameter. In embodiments, such as stents having double-walled flanges as first and second retention members comprising an axially inward wall and axially outward wall, where a portion of the inward wall bends toward a vertical center plane of the stent, the length of the cylindrical saddle region may be measured as (i) the length along the elongate body between the beginning of the inward walls of each of the flanges, or (ii) the length along the body that is the shortest distance between flanges at any points along the inward walls when the stent is expanded, but not deployed in tissue, or (iii) the length along the body that is the shortest distance between flanges at any points along the inward walls when the stent is expanded and deployed in tissue. In many embodiments, a cylindrical saddle region, including under the conditions (i)-(iii) above, may have a length within the range inclusive of 5-150 mm in the expanded configuration, although in some instances the cylindrical saddle region (such as region 128 of FIGS. 1-2) may have a length in the range inclusive of 5-35 mm in the expanded configuration. Exemplary lengths of the cylindrical saddle region of devices for gastrointestinal stenting or drainage in the expanded configuration may include lengths within a range inclusive of 10-30 mm, 15-20 mm, 10-20 mm, 10-15 mm, or 5-10 mm.

In many embodiments, a diameter of the cylindrical saddle region in the expanded configuration may be greater than a diameter of the elongate body in the constrained configuration. For example, a diameter of the cylindrical saddle region (such as region 128 of FIGS. 1-2) in the expanded configuration may be within the range inclusive of 3-40 mm. In some embodiments, the diameter of the cylindrical saddle region 128 in the expanded configuration may be within inclusive ranges of 5-25 mm, 5-20 mm, 5-15 mm, or 10-20 mm, for example, 5 mm, 10 mm, 15 mm, or 20 mm. In various embodiments, the diameter of the cylindrical saddle region 128 in the expanded configuration may be 3-5 times greater than a corresponding diameter of the stent in the constrained configuration, although in several embodiments, the diameter of the cylindrical saddle region 128 in the expanded configuration may be 3-10 times greater than the corresponding diameter of the stent in the constrained configuration.

Referring again to FIGS. 1-2, the first and second retention members 114, 124 may extend radially outward from an outer circumference of the elongate body 110 in the expanded configuration to define double-walled flanges with respective inward wall surface 114a, outward wall surface 114b, inward wall surface 124a, and outward wall surface 124b. For example, inward wall surface 114a may be an axially inward wall of a first flange, outward wall surface 114b may be an axially outward wall of the first flange, inward wall surface 124a may be an axially inward wall of a second flange, and outward wall surface 124b may be an axially outward wall of the second flange. A radially outwardmost edge 114c may extend between and connect inward wall surface 114a and outward wall surface 114b. A radially outwardmost edge 124c may extend between and connect inward wall surface 124a and outward wall surface 124b. A radially outwardmost edge may be offset from a vertical plane along the longitudinal axis extending between a beginning of an inward wall surface and an ending of the outward wall surface of a retention member, or offset from a center point of a distance extending between a cylindrical saddle region and an endmost projection or lip. A radially outwardmost edge may comprise a diameter greater than a diameter of the cylindrical saddle region. In various embodiments, a radially outwardmost edge may define a diameter of a respective retention member.

In embodiments, a diameter of the first retention member and/or a second retention member (such as members 114, 124 of FIGS. 1-2) may be within the range inclusive of 5-40 mm. Other exemplary retention member diameters may be within a range inclusive of 15-40 mm or 15-35 mm. In many embodiments, a diameter of a retention member may be set to have a particular offset from a diameter of the cylindrical saddle region in the expanded configuration. For example, stents may be configured to include a 3-20 mm difference between a diameter of the cylindrical saddle region and a diameter of the first retention member and/or a second retention member in the expanded configuration. In other examples, the first retention member and/or the second retention member may be configured to have a diameter that is 1-5 times greater than the diameter of the cylindrical saddle region in the expanded configuration. For example, for a device with the cylindrical saddle region having a diameter of 10 mm in an expanded configuration, the first retention member and/or a second retention member may have a diameter within inclusive ranges of 13-30 mm, 15-25 mm, or 16-20 mm. In another example, a stent with the cylindrical saddle region in the expanded configuration having a diameter of 20 mm may have one or more retention members with a diameter within the inclusive range of 23-40 mm. It will be understood that some embodiments may include greater or lesser offsets between the diameter of the cylindrical saddle region and the larger diameter of the first retention member and/or the second retention member.

Referring again to FIGS. 1-2, the first retention member 114 may have a same or different axial width as the second retention member 124, wherein the axial width of a retention member may be measured as a distance along the longitudinal axis between an inward wall and outward wall of a respective retention member, inclusive of the radially outwardmost edge. In some embodiments, the width of the first retention member 114 and/or the second retention member 124 in the expanded configuration may be within the inclusive range of 0.5-10.0 mm. Other embodiments may include a smaller and/or greater width of the first retention member and/or the second retention member, such as within the inclusive rages of 0.5-6 mm, 2-6 mm, or 3-7 mm. In some embodiments, a retention member may have a constant width. In other embodiments, a width of a retention member may vary along a vertical plane.

Figure 2:
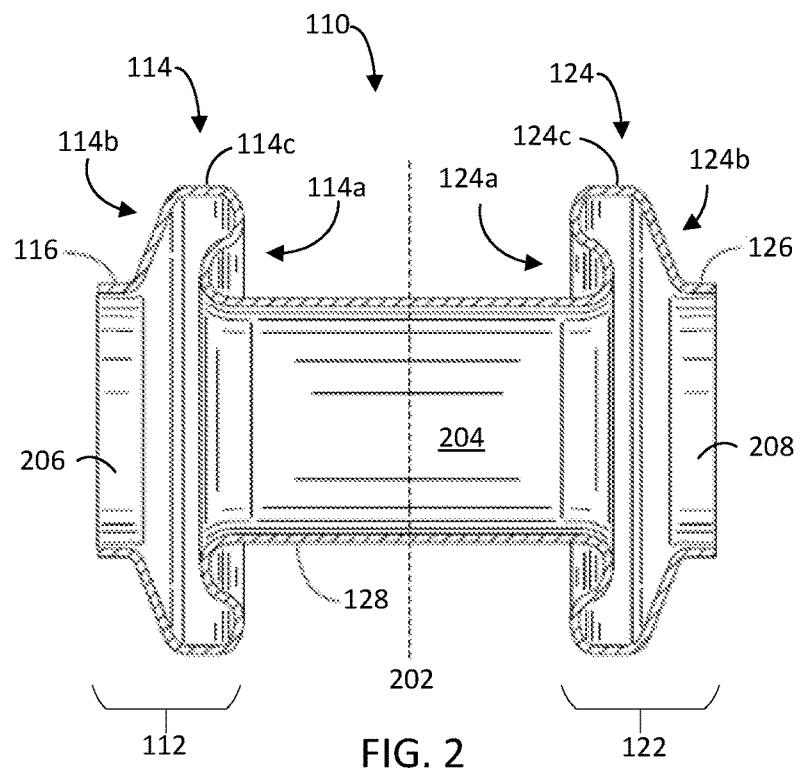
FIG. 2 illustrates a cross-sectional view of a medical device according to one or more embodiments described herein.

As shown in FIGS. 1-2, the outward wall surface 114b of the first retention member 114 may extend away from the vertical center plane of the cylindrical saddle region 128 substantially along the longitudinal axis into a projection 116, or lip, at an axially outermost end of the first retention member 114 of the elongate body 110. The outward wall surface 124b of the second retention member 124 may extend away from the vertical center plane of the cylindrical saddle region 128 substantially along the longitudinal axis into a projection 126, or lip, at an axially outermost end of the first retention member 114 of the elongate body 110. In some embodiments, the projection 116 and/or projection 126 may have a length within the range inclusive of 0-3 mm in the expanded configuration, such as within the inclusive ranges of 0.5-2.5 mm or 1.0-1.5 mm. The projection 116 and/or a projection 126 may define a lumen, such as a flange lumen contiguous with the cylindrical saddle region, with a diameter greater than or equal to the diameter of the lumen defined by the cylindrical saddle region 128, or saddle lumen. In various embodiments, a lip, or projection, may comprise a flange lumen diameter in the expanded configuration that is at least 0.5-2.0 mm wider than the diameter of a corresponding cylindrical saddle region 128 in an expanded configuration, for example, within the diameter range inclusive of 3.5-42 mm for a saddle diameter within the range inclusive of 3-40 mm. As further exemplary inclusive ranges, for a corresponding cylindrical saddle region diameter of 10 mm in the expanded configuration, a lip may have a diameter of 11-14 mm. For a corresponding cylindrical saddle region diameter of 15 mm in the expanded configuration, a lip may have a diameter of 16-19 mm. In another example, a cylindrical saddle region diameter of 20 mm in the expanded configuration may correspond with a lip diameter of 21-24 mm. The projection 116 and/or projection 126 may be formed contiguously with the retention members 114, 124 and with the saddle lumen 128. The projection 116 and/or the projection 126 may be parallel to the longitudinal axis of the cylindrical saddle region. Alternatively, or additionally, the projection 116 and/or the projection 126 may be non-parallel to the longitudinal axis. For example, the projection 116 and/or the projection 126 may extend radially outward or inward along the longitudinal axis. A radially outward extension of the projection 116 and/or of the projection 126 may encourage flow through a lumen thereof, for example, by acting as a funnel into the lumen. A radially inward extension of the projection 116 and/or of the projection 126 may discourage flow through a lumen thereof, for example, by defining a smaller entrance thereof.

Various embodiments may include total stent lengths ranging from 5-60 mm in the expanded configuration. For example, exemplary deployed stents may have lengths of 10-50 mm or 10-35 mm.

In various embodiments, an angle of the retention members relative to the circumference and longitudinal axis of the elongate body may assume various degrees or may change degrees of orientation (as compared to a retention member with perpendicular walls) along the axially inward and/or outward walls of the retention members creating inflection points in the walls of the retention members. For example, as shown in the cross-sectional view of the stent of FIG. 2, the outward wall surface 114*b* and/or the outward wall surface 124*b* may comprise at least one portion of the axially outward walls extending or bending away from a vertical center plane 202, or midline, of the longitudinal axis of the cylindrical saddle region 128. Additionally, or alternatively, the outward wall surface 114*b* and/or the outward wall surface 124*b* may comprise at least one portion of the axially outward walls extending or bending towards the vertical center plane 202. Similarly, the inward wall surface 114*a* and/or the inward wall surface 124*a* may comprise at least one portion of the axially inward walls extending or bending away from the vertical center plane 202 of the longitudinal axis of the cylindrical saddle region 128. Additionally, or alternatively, the inward wall surface 114*a* and/or the inward wall surface 124*a* may comprise at least one portion of the axially inward walls extending or bending towards the vertical center plane 202. In various embodiments, the inward wall surface 114*a* and the outward wall surface 114*b* of retention member 114 may be non-parallel with respect to each other, and/or the inward wall surface 124*a* and the outward wall surface 124*b* of retention member 124 may comprise non-parallel surfaces with respect to each other.

A lumen 204 may extend throughout a longitudinal length of the cylindrical saddle region 128. The saddle region lumen 204 may include dimensions suited for different purposes, for example, as described above.

One or more components illustrated with respect to FIG. 2 may comprise one or more similar aspects as respective structures illustrated and/or described with respect to FIG. 1. For example, an elongate body of the stent of FIG. 2 may be similar to or the same as the elongate body 110 described with respect to FIG. 1.

While FIGS. 1-2 illustrate the stent comprising both a first retention member and a second retention member including double-walled flange structures, it will be understood that a stent may comprise only one of a first or second retention member. Additionally, or alternatively, a stent may comprise a first retention member and/or a second retention member including an alternative configuration, such as a flared geometry, a funnel, an obstruction component, a widened structure, or another configuration for facilitating flow through the stent.

The projection 116 in the expanded configuration may define a first projection lumen 206, which may have a diameter that is at least as large as the diameter of the lumen 204. The projection 126 in the expanded configuration may define a second projection lumen 208, which may have a diameter that is at least as large as the diameter of the lumen 204. The diameter of the first projection lumen 206 may be the same as or different from the diameter of the second projection lumen 208. For example, exemplary diameters of the first projection lumen 206 may be defined by the exemplary diameters of the first projection 116 as described with respect to FIG. 1, exemplary diameters of the second projection lumen 208 may be defined by the exemplary diameters of the second projection 126 as described with respect to FIG. 1, or both. The various dimensions outlined above in connection with the stent of FIG. 1, e.g., the constrained configuration length and diameter, the expanded configuration overall stent length, saddle region length and diameter, retention member width and diameter, and projection length, may be applicable to the stent of FIG. 2, and may be applicable to any stent with a retention member configuration as described below with respect to FIGS. 3A-3F.

FIGS. 3A-3F illustrate alternative configurations for a cross-sectional profile of a double-walled flange structure as second retention member 124 in the expanded configuration. For each of FIGS. 3A-3F, the cylindrical saddle region 128 is depicted as extending from a left side of the illustration into retention member 124. The retention member 124 is depicted as extending into the projection 126 on the right side of the illustration.

Figure 3A:
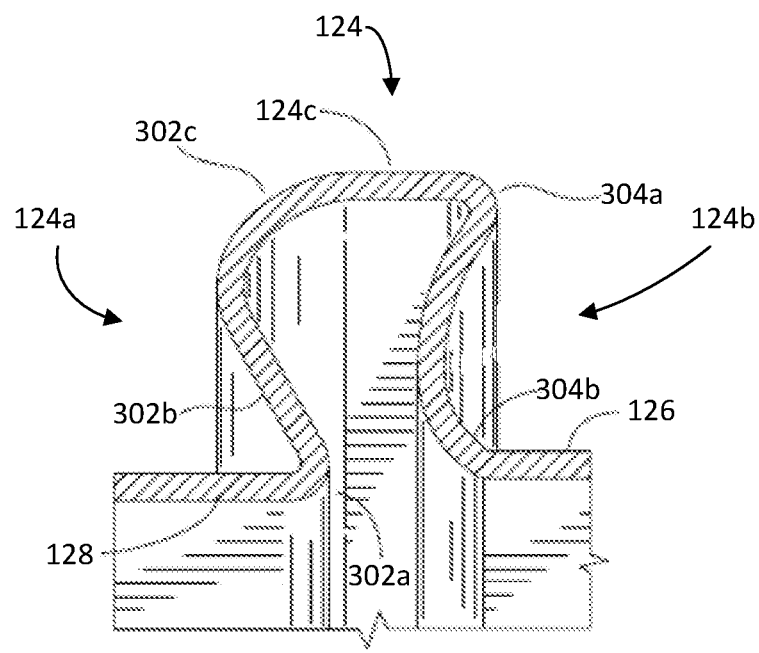
FIGS. 3A-3F illustrate alternative retention member configurations according to various embodiments described herein.
Figure 3B:
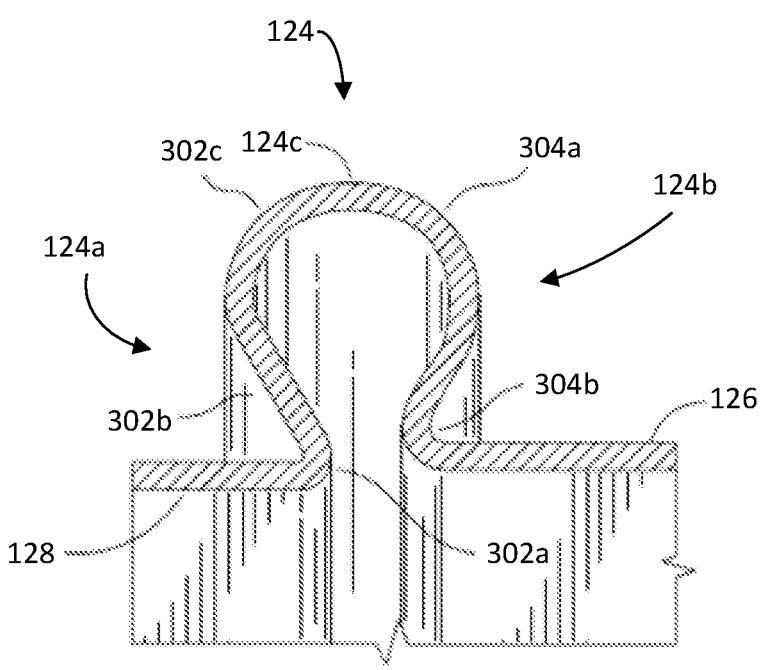
Figure 3C:
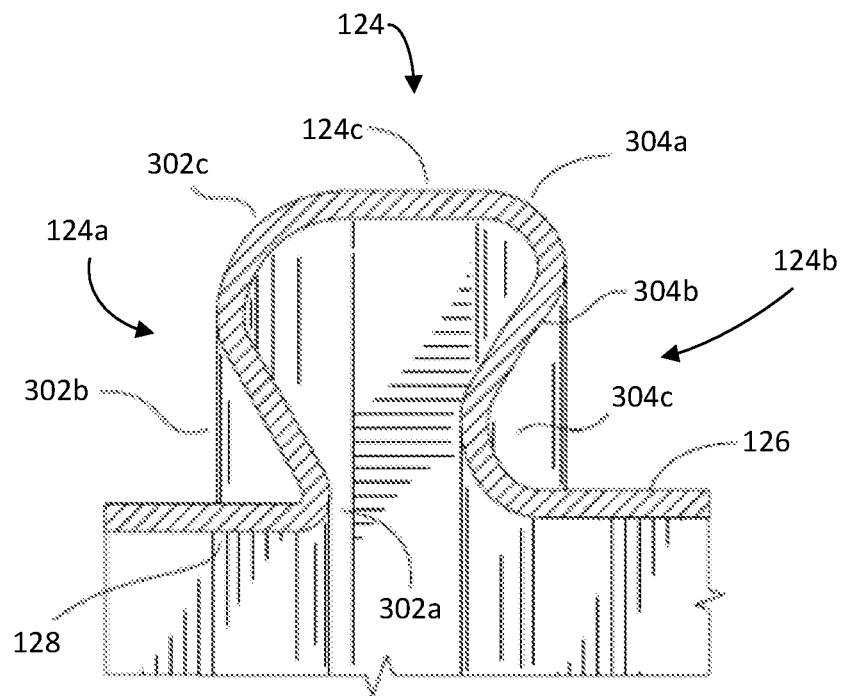

A configuration of a flange structure as described with respect to FIGS. 3A-3F may be applied to any of the embodiments described herein. For example, the first retention member 114 as described with respect to FIG. 1, the second retention member 124 as described with respect to FIG. 1, or both, may have a configuration as described with respect to FIGS. 3A-3F. Accordingly, embodiments may comprise multiple retention members with the same or with different configurations. For example, the first retention member 114 may comprise a configuration as illustrated in FIG. 3A and the second retention member 124 may comprise a configuration as illustrated in FIG. 3C. Any combination of the described configurations is within the scope of the present disclosure.

Alternatively, or additionally, various embodiments may comprise one of the first retention member 114 or the second retention member 124 and an alternative configuration at an opposite end. For example, various embodiments may include as an alternative configuration a flange with walls perpendicular to the respective cylindrical saddle region 128, a flared retention member, a bulbous retention member, a ramped retention member, a curled retention member, a folded retention member, or another configuration (not shown). Several embodiments may include one or more components for managing material flow therethrough. For example, various embodiments may include a valve, barrier member, funnel, tube, or other structure useful for managing a flow therethrough.

In various embodiments of a medical device, at least a portion of an inward wall surface of a retention member, an outward wall surface of a retention member, or both, may comprise at least one curved surface, straight surface, angle, inner radial circumference, outer radial circumference, surface extending or bending toward a vertical center plane of a cylindrical saddle region or central region of the medical device, surface extending or bending away from the vertical center plane of the saddle or central region of the medical device, surface perpendicular to a longitudinal axis of the cylindrical saddle region, surface parallel to the longitudinal axis of cylindrical saddle region, or any combination thereof.

An inward wall surface and an outward wall surface of a retention member may comprise non-parallel surfaces, as illustrated by way of the examples of FIGS. 3A-F. In various embodiments, a retention member may comprise asymmetrical inward and outward wall surfaces. For example, a cross-sectional profile of the first retention member 114 or of the second retention member 124, or both, may be asymmetrical along a longitudinal axis of cylindrical saddle region 128. In some embodiments, asymmetrical wall surfaces may each have a shape and/or strength, such as a retentive strength, which may respectively accommodate for interaction with tissues of appropriate geometries and/or mechanical characteristics/interactions.

A portion of a retention member with the greatest external diameter may comprise a radially outwardmost edge that may connect, couple, and/or extend between an inward wall surface and an outward wall surface of the retention member. For example, the radially outwardmost edge (e.g., 124c of FIGS. 1-3F) may comprise a ridgeline along a curved meeting of the inward wall surface 124a and the outward wall surface 124b, such as in FIG. 3B, or a radially outwardmost edge may comprise one or more portions parallel to the longitudinal axis of the cylindrical saddle region 128, such as in FIGS. 3A, 3C, 3D, and 3E. The radially outwardmost edge 124c may or may not be centered above a length along the longitudinal axis between a beginning of an inward wall surface of a retention member and an end of an outward wall surface.

In various embodiments, at least a portion of a retention member may comprise a concave surface, such as outward wall surface 124b as illustrated in FIG. 3A. In several embodiments, a concave surface or portion of a retention member may bend away from a vertical center plane of the cylindrical saddle region along the longitudinal axis (e.g., vertical center plane 202 of FIG. 2). In various embodiments, at least a portion of a retention member may comprise a convex surface, for example, inward wall surface 124a as illustrated in FIG. 3A. In several embodiments, a convex surface or portion of a retention member may bend towards a vertical center plane of the cylindrical saddle region along the longitudinal axis (e.g., vertical center plane 202 of FIG. 2). An inward wall surface and/or outward wall surface of respective first and second retention members, in any combination thereof, with a configuration including a portion non-perpendicular to the cylindrical saddle region may increase a resistance of the respective retention member to deformation, thereby increasing a pull-out strength of the retention member with respect to a flange comprising only surfaces perpendicular to a longitudinal axis of the cylindrical saddle region. Additionally, or alternatively, inward wall surfaces may engage and maintain apposition of tissue walls with less trauma to the tissue walls and with greater resistance to motion than a respective surface perpendicular to a cylindrical saddle region. Accordingly, a stent with retention members according to embodiments of the present disclosure may be subject to less migration than a respective surface perpendicular to a cylindrical saddle region.

For example, as illustrated in FIG. 3A, an elongated body may extend from the cylindrical saddle region 128 into a retention member. While FIG. 3A illustrates second retention member 124 as a double-walled flange structure, it will be recognized that the first retention member 114 may comprise the configuration illustrated in FIG. 3A. For example, the first retention member 114 may comprise a corresponding double-walled flange structure.

Additionally, or alternatively, either of the first retention member 114 or the second retention member 124 may comprise an alternative configuration.

With respect to FIG. 3A, the cylindrical saddle region 128 may extend into the inward wall surface 124a, which in this example comprises three portions: portion 302a, portion 302b, and portion 302c. The cylindrical saddle region 128 may extend into a concave surface of portion 302a, which may extend into portion 302b. The portion 302b comprises a straight edge which extends at an angle of less than 90 degrees towards a vertical center plane of the cylindrical saddle region (not shown). In some embodiments, an inward wall surface may extend a distance of 0.0-5.0 mm along a longitudinal axis of the cylindrical saddle region towards a vertical center plane thereof. For example, portion 302b may extend 0.5-1.5 mm towards the vertical center plane of the cylindrical saddle region 128. However, in other embodiments in line with the present disclosure, an inward wall surface may extend a greater distance along the longitudinal axis of the cylindrical saddle region towards a vertical center plane thereof. The portion 302c comprises a convex curve, which extends between the portion 302b and the radially outwardmost edge 124c. The radially outwardmost edge 124c may comprise a portion parallel to a surface of the cylindrical saddle region 128. The radially outwardmost edge 124c may extend into the outward wall surface 124b, which in the example of FIG. 3A may comprise a portion 304a and a portion 304b. The portion 304a may comprise a convex surface. In various embodiments, an interior radius of curvature between an inward wall surface and a radially outwardmost edge may be greater than an interior radius of curvature between the radially outwardmost edge and an outward wall. For example, as illustrated in FIG. 3A, the portion 302b may have a greater internal radius of circumference than portion 304a. However, it will be recognized that alternative embodiments may include varying relative radii of circumferences between portions. The portion 304a may extend into the portion 304b, which may comprise a concave surface. The portion 304b may extend into the projection 126, as described elsewhere herein. One or more convex and/or concave surfaces may include the same or various angles of completion of curvature, radii of circumference, lengths, other feature, or any combination thereof.

Regarding the example embodiment illustrated in FIG. 3B, a retention member may comprise similar portions 302a, 302b, and 302c as described with respect to FIG. 3A. However, portion 304a as illustrated in FIG. 3B may comprise a larger radius of curvature than as illustrated in FIG. 3A. In FIG. 3B, portion 304a may comprise varying radii of curvature along its length. In some embodiments, portion 304a or other portion may comprise a non-uniform and/or otherwise undulating curve. Portion 304b, as illustrated in FIG. 3B, may comprise a concave portion.

FIG. 3C illustrates another exemplary embodiment, in which a retention member may comprise similar portions 302a, 302b, and 302c as described with respect to FIG. 3A and/or FIG. 3B. However, portion 304a as illustrated in FIG. 3C may comprise a larger radius of curvature than as illustrated in FIG. 3A. In FIG. 3C, portion 304b may comprise a straight edge extending from radially outwardmost edge 124c and portion 304a back towards the cylindrical saddle region 128. The portion 304b may extend into a portion 304c, which is illustrated in FIG. 3C as comprising a concave portion. Portion 304c may extend into the projection 126. In many embodiments, an angle directed to an exterior of the second retention member 124 and defined by portion 304b and projection 126, or an angle of portion 304c, may be less than 90 degrees.

Figure 3D:
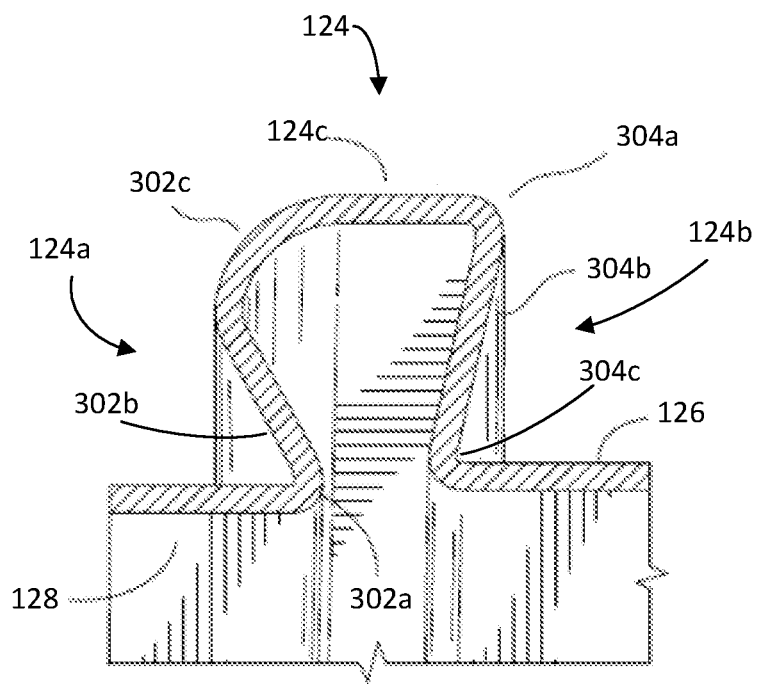

An additional exemplary embodiment is illustrated in FIG. 3D. In FIG. 3D, the portion 302a may comprise a concave curve which extends into a straight edge of portion 302b. The portion 302b may extend into a convex curve of portion 302c, which may in turn extend into the radially outwardmost edge 124c. The radially outwardmost edge 124c may extend into the portion 304a, which may comprise a convex curve. The portion 304a may extend into a straight edge of portion 304b, which may in turn extend into the portion 304c, which may comprise a concave segment. The portion 304c may extend into the projection 126. However, one or more portions 302a, 302c, 304a, and/or 304c may comprise smaller radii of curvature, e.g., as illustrated with respect to the concave curve portion 304c in FIG. 3D compared to the concave curve portion 304c in FIG. 3C. In some embodiments, a concave or convex curve of at least one portion may comprise a tight enough radius of curvature to comprise a crease or other fold.

Figure 3E:
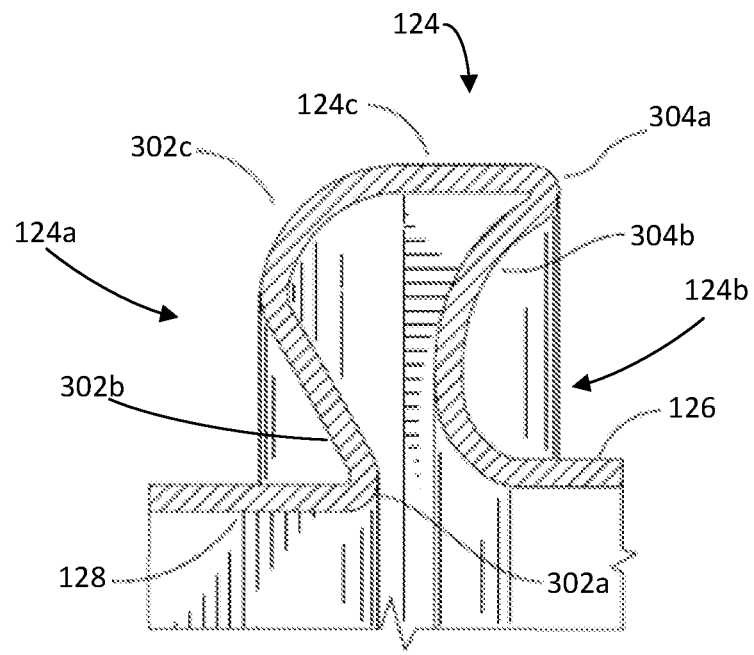

FIG. 3E illustrates another exemplary embodiment, in which portions 302a, 302b, 302c, 304a, and/or 304b may comprise one or more similarities as corresponding portions described with respect to at least one of FIGS. 3A-D. However, in FIG. 3E, the curves of portion 304a and portion 304b comprise smaller radii of curvature than as illustrated for the curves of portions 304a and 304b in FIG. 3A.

Figure 3F:
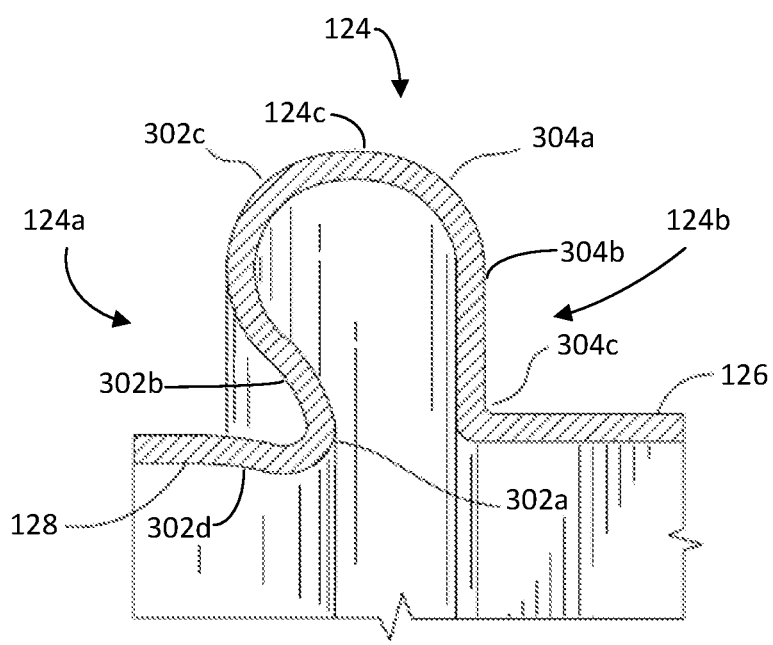

FIG. 3F illustrates another exemplary embodiment, in which a retention member may comprise similar portions 302a, 302b, and 302c as described with respect to at least one of FIGS. 3A-E. Portion 302a, as illustrated in FIG. 3F, may comprise a larger radius of curvature than as illustrated in FIG. 3A. For example, a portion, such as portion 302a as illustrated in FIG. 3F, may comprise a radius of curvature of 1-3 mm. In some embodiments, portion 302a and/or 302c may comprise a radius of curvature of 1.5-2.1 mm. In FIG. 3F, portion 302a may comprise varying radii of curvature along its length. As illustrated in FIG. 3F, portion 302a may extend, or dip, into a narrower radius than the respective cylindrical saddle region 128. A portion 302d may extend between the cylindrical saddle region 128 and the portion 302a or 302d may be considered an extension of the cylindrical saddle region leading into the beginning of portion 302a and the beginning of the inward wall surface 124a. In some embodiments, portion 302a or other portions may comprise a non-uniform and/or otherwise undulating curve. Portion 304b, as illustrated in FIG. 3F, may comprise a straight portion perpendicular to the longitudinal axis of the cylindrical saddle region 128. Portion 304c may comprise a concave surface extending into the projection 126. A portion may comprise a small enough radius of curvature as to constitute a right angle or a relatively right angle. For example, a portion, such as portion 304c as illustrated in FIG. 3F, may comprise a radius of curvature of 0.0-0.5 mm, for example, 0.1-0.3 mm.

While various portions are described with respect to FIGS. 3A-3F, it will be appreciated that various embodiments may comprise one or more similarities and/or differences from the illustrated examples. For example, an inward wall surface 114a, outward wall surface 114b, inward wall surface 124a, and/or outward wall surface 124b may comprise more or fewer portions, and any portion thereof may comprise at least one concave section, convex section, straight edge, or any combination thereof. A portion may extend toward a first or second end of the device, perpendicular to a surface of a cylindrical saddle region, parallel to a surface of a cylindrical saddle region, at another angle with respect to a surface of a cylindrical saddle region, or any combination thereof. Furthermore, dimensions and/or orientations of any of the portions described with respect to FIGS. 3A-F may be applied to other portions described therewith, alternatively or in combination, or with portions and/or retention member profiles otherwise with the scope of the present disclosure.

In several embodiments, smaller radii of curvature in portions may contribute to a higher retentive strength of the corresponding retention member. For example, the configuration illustrated in FIG. 3E may comprise a greater resistance to a deformation of second retention member 124 than the respective configuration of FIG. 3A. Accordingly, embodiments may be configured in accordance with various retention member strength requirements as necessitated by at least one particular procedure, tissue, or other consideration.

Figure 4:
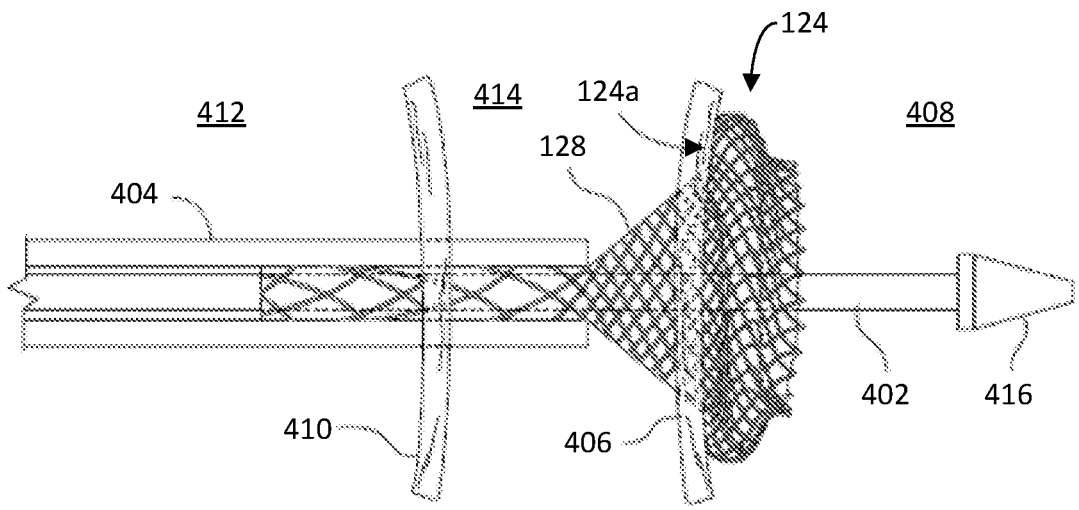
FIG. 4 illustrates aspects of delivery of a medical device according to one or more embodiments described herein.

FIG. 4 illustrates by way of example aspects of a delivery method for a medical device as described herein.

The medical device may be disposed in a constrained configuration between an inner member 402 and an outer sheath 404 of a tissue-penetrating element. For example, in a constrained configuration, one or more of the first retention member 114, the second retention member 124, or the cylindrical saddle region 128 may be restricted to a smaller outer diameter, as described with respect to FIGS. 1-3, compared to those features in an expanded or unconstrained configuration. A sharpened end 416 of the tissue penetrating element may be included to advance through a tissue layer 410 from a first body lumen 412. The sharpened end 416 of the tissue penetrating element may be advanced through a tissue layer 406 and into a second body lumen 408. Additionally, or alternatively, the tissue penetrating element may comprise an electrically conductive tip for advancing through the tissue layer 410 and/or the tissue layer 406. In various embodiments, a gap space 414 may exist between the tissue layer 410 and the tissue layer 406 prior to the deployment of the medical device (e.g., stent).

With the end of the tissue penetrating element advanced through the tissue layer 406, the outer sheath 404 may be proximally retracted with respect to the inner member 402 or the inner member 402 may be distally extended with respect to the outer sheath 404, thereby allowing a distal end of the medical device to move from the constrained configuration to an unconstrained configuration. In particular, the distal end of the medical device may expand into the second retention member 124.

The medical device may be positioned such that a portion of the inward wall surface 124a of the second retention member 124 contacts the tissue layer 406. The tissue penetrating element may be proximally retracted through the tissue layer 406 so that the second retention member 124 remains in the second body lumen 408. The tissue penetrating element may be proximally retracted through the tissue layer 410 (not shown).

After deploying the second retention member, the medical device may be retracted proximally a distance, e.g., a predetermined distance that may be indicated by a visual (such as colored band) and/or imageable (such as radiopaque band) marker(s) on the device, along with the entire assembly of inner member and outer sheath, so that the first retention member remains constrained between the two and is not prematurely deployed (e.g. in the gap space 414). The action of proximally retracting the entire assembly, once the second (or distal in this instance) retention member 124 is deployed, may also act to draw tissue layers 410, 406 into apposition or further into apposition with each other. When the device is retracted a sufficient distance to clear the tissue layer 410, the outer sheath 404 may be proximally retracted with respect to the inner member 402 or the inner member 402 may be distally extended with respect to the outer sheath 404, thereby allowing a proximal end of the medical device to move from the constrained configuration to an unconstrained configuration. In particular, the proximal end of the medical device may expand into the first retention member 114.

Figure 5:
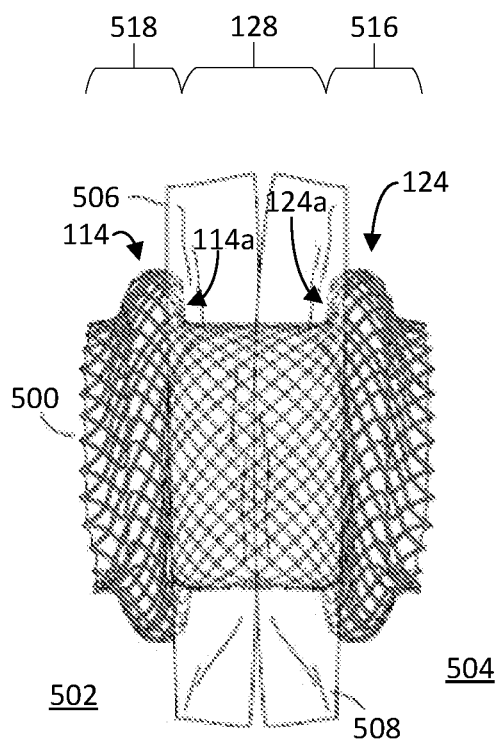
FIG. 5 illustrates a medical device disposed in tissue according to one or more embodiments described herein.

FIG. 5 illustrates a cross section of a fully delivered stent of the present disclosure. For example, the stent of FIG. 5 may be a stent as described with respect to FIGS. 1-4. Various components of the stent may be similar to components described above. The stent may be positioned within a patient such that the inward wall surface 114a of the first retention member 114 contacts a tissue wall 506 and the outward wall surface 124a of the second retention member 124 contacts a tissue wall 508, with the cylindrical saddle region 128 extending therebetween. Apposing tissue layers may be walls of the same or of different tissues. For example, the tissue wall 506 may correspond to the tissue layer 410 and the tissue wall 508 may correspond to the tissue layer 406 as described with respect to FIG. 4. In some embodiments, the first retention member 114 and the second retention member 124 may contact the tissue wall 506 of a first tissue and the tissue wall 508 of a second tissue so that the first tissue and the second tissue interact at a tissue interface. In some embodiments, the first retention member 114 and the second retention member 124 may interact with the tissue wall 506 and the tissue wall 508 to cause an interaction of the respective tissue walls at an interface so as to close and/or shorten a width of a space therebetween. For example, a width of the gap space 414 as described with respect to FIG. 4 may be decreased and or eliminated. In some embodiments, at least one additional tissue (not illustrated) may be positioned between a tissue of the first tissue wall 506 and a tissue of the second tissue wall 508. A lumen extending through the first retention member 114, second retention member 124, and cylindrical saddle region 128 may therefore provide an open interior passage between the first body lumen 502 and the second body lumen 504. The stent may be partially or fully covered, for example, to prevent fluid draining from the second body lumen to first body lumen from leaking through the retention members and/or saddle region of the stent to within the gap space between the tissue walls.

As described by way of example with respect to FIG. 5, the stent may be disposed in a constrained configuration between an inner member and an outer sheath of a tissue-penetrating element. For example, in a constrained configuration, one or more of the first retention member 114, the second retention member 124, or the cylindrical saddle region 128 may be constrained to a smaller outer diameter. A sharpened end of the tissue penetrating element may be advanced through a tissue wall and into the second body lumen 504. Additionally, or alternatively, the tissue penetrating element may comprise an electrically conductive tip for advancing through a tissue wall. The distal portion 516 of the stent may then be advanced distally beyond the lumen of the tissue-penetrating element such that the second retention member 124 is deployed within the second body lumen 504 and the inward wall surface 124a placed in contact with the tissue wall 508. The tissue-penetrating element may then be proximally retracted along with the proximal end of the constrained stent such that the proximal portion of the stent is disposed on a proximal side of tissue wall 506. The proximal portion 518 of the stent may then be deployed in the first body lumen 502 such that the first retention member 114 is unconstrained from sheath and expands within the first body lumen 502 with the inward wall surface 114a contacting the tissue wall 506.

Alternatively, in the methods above, a separate instrument with a sharpened tip may be advanced along the path above and into the second body lumen 504, 408 to create a path, a guidewire put in place and the separate instrument withdrawn over the guidewire, and a stent, according to the various embodiments described above, loaded on a delivery catheter inserted over the guidewire, and the stent then deployed according to the steps outlined above.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

The invention claimed is:

1. A stent, comprising:
an elongate body configured to be expandable between a first constrained configuration and a second unconstrained configuration,
the elongate body in the second unconstrained configuration including a first retention member extending radially outwardly from the elongate body, a second retention member extending radially outwardly from the elongate body, and a saddle region defining a lumen extending along a longitudinal axis therebetween;
wherein:
at least one of the first retention member or the second retention member comprises a double-walled flange having an axially inward wall, an axially outward wall spaced apart from the axially inward wall, and a radially outwardmost edge extending therebetween; and
at least a portion of the inward wall of the at least one of the first retention member or the second retention member bends towards a vertical center plane of the saddle region along and transverse to the longitudinal axis such that a radially-outer portion of said at least a portion is closer to the vertical center plane than a radially-inner portion of said at least a portion.

2. The stent of claim 1, wherein the inward wall and the outward wall of the first retention member or the second retention member, or both, comprise non-parallel surfaces.

3. The stent of claim 1, wherein at least a portion of the outward wall bends away from the vertical center plane of the saddle region along the longitudinal axis.

4. The stent of claim 1, wherein the outward wall comprises a concave portion bending away from the vertical center plane of the saddle region along the longitudinal axis.

5. The stent of claim 1, wherein the inward wall or the outward wall, or both, comprises a straight edge.

6. The stent of claim 1, wherein the inward wall comprises a convex portion bending away from the vertical center plane of the saddle region along the longitudinal axis.

7. The stent of claim 1, wherein the outward wall comprises a convex portion bending toward the vertical center plane of the saddle region along the longitudinal axis.

8. The stent of claim 1, wherein an axially outermost end of the first retention member or an axially outermost end of the second retention member, or both, extends away from the vertical center plane of the saddle region into a lip defining a lumen of the double-walled flanges, the flange lumens contiguous with the saddle region lumen.

9. The stent of claim 8, wherein the lip comprises an interior diameter equal to or wider than an interior diameter of the saddle region lumen.

10. The stent of claim 1, wherein the radially outwardmost edge comprises a diameter greater than a diameter of the saddle region.

11. The stent of claim 1, wherein the radially outwardmost edge comprises a cylindrical portion parallel to the longitudinal axis.

12. The stent of claim 1, wherein an interior radius of curvature between the inward wall and the radially outwardmost edge is greater than an interior radius of curvature between the radially outwardmost edge and the outward wall.

13. The stent of claim 1, wherein the elongate body comprises a braid of one or multiple wires.

14. The stent of claim 1, further comprising a circumferential covering extending fully or partially along a length of the elongate body.

15. A stent, comprising:
a tubular structure having a constrained configuration and an expanded configuration, the tubular structure in the expanded configuration including a first end of the tubular structure expanded into a first double-walled flange, a second end of the tubular structure expanded into a second double-walled flange, and a central region defining a lumen extending along a longitudinal axis therebetween;
wherein:
at least one of the first double-walled flange or the second double-walled flange comprises an axially inward wall extending radially outwardly from the elongate body and an axially outward wall extending radially outwardly from the elongate body and spaced apart from the axially inward wall, at least a portion of the inward wall bending towards a vertical center plane of the central region along the longitudinal axis as said inward wall extends radially outwardly; and
a cross-sectional profile of at least one of the first double-walled flange or the second double-walled flange along a plane parallel to the longitudinal axis is asymmetrical.

16. The stent of claim 15, wherein the inward wall and the outward wall of the first retention member or the second retention member, or both, comprise non-parallel surfaces.

17. The stent of claim 15, wherein the inward wall comprises:
a first curved portion bending toward the vertical center plane of the central region along the longitudinal axis; and
a second curved portion bending away from the vertical center plane of the central region along the longitudinal axis.

18. The stent of claim 15, wherein the inward wall or the outward wall, or both, comprises a straight edge.

19. A stent, comprising:
a cylindrical body having a constrained configuration and an expanded configuration, wherein in the expanded configuration the cylindrical body comprises:
a first retention member, a second retention member, a saddle region defining a lumen extending along a longitudinal axis between the first retention member and the second retention member;
wherein:
at least one of the first retention member or the second retention member comprises double-walled flanges including an axially inward wall extending radially outwardly from the elongate body and an axially outward wall extending radially outwardly from the elongate body and spaced apart from the axially inward wall, at least a portion of the inward wall extending radially outwardly and bending towards a vertical center plane of the saddle region along the longitudinal axis; and
the inward wall and the outward wall of at least one of the first retention member or the second retention member comprises non-parallel surfaces.

20. The stent of claim 19, wherein the inward wall comprises:
a first curved portion bending toward the vertical center plane of the saddle region along the longitudinal axis; and
a second curved portion bending away from the vertical center plane of the saddle region along the longitudinal axis.

* * * * *